United States Patent [19]
Meyer

[11] 4,014,644
[45] Mar. 29, 1977

[54] TOLANE COMPOUNDS
[75] Inventor: Hans Rudolf Meyer, Binningen, Switzerland
[73] Assignee: Ciba-Geigy Corporation, Ardsley, N.Y.
[22] Filed: June 10, 1975
[21] Appl. No.: 585,543
[30] Foreign Application Priority Data
June 12, 1974 Switzerland .................. 8031/74
June 12, 1974 Switzerland .................. 8037/74
[52] U.S. Cl. .................................. 8/1 W; 260/247; 260/290 R; 260/293.51; 260/501.21; 260/505 R
[51] Int. Cl.² ........................................ D06P 1/38
[58] Field of Search ........... 260/505 R, 247, 290 R, 260/293.51, 501.21; 8/1 W

[56] References Cited
OTHER PUBLICATIONS
"Helvetica Chimica Aeta", vol. 50, (1967), pp. 906–956.
"Helvetica Chimica Aeta", vol. 52, (1969), pp. 2521–2554.

Primary Examiner—James O. Thomas, Jr.
Assistant Examiner—A. Siegel
Attorney, Agent, or Firm—Joseph G. Kolodny; Edward McC. Roberts; Prabodh I. Almaula

[57] ABSTRACT
New tolane compounds, a novel process for their manufacture as well as their use as optical brighteners for high-molecular organic materials, particularly polyamides and cellulose are disclosed.

6 Claims, No Drawings

TOLANE COMPOUNDS

The present invention relates to tolane compounds, a process for their manufacture and their use as optical brighteners for high-molecular organic materials.

These new tolane derivatives correspond to the formula

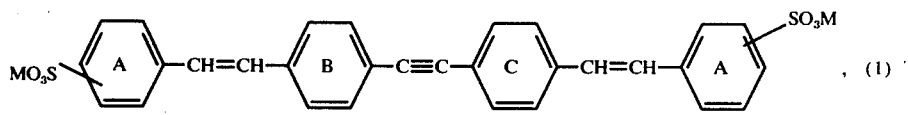

wherein M denotes hydrogen or a salt-forming cation, and the benzene nuclei A, B and C can contain non-chromophoric substituents.

Examples of non-chromophoric substituents are alkyl having 1 to 4 carbon atoms, the methyl group being preferably in the 3-position, chlorine, alkoxy having 1 to 4 carbon atoms, phenoxy, alkylmercapto having 1 to 4 carbon atoms, phenylmercapto or sulpho.

Two adjacent substituents can also conjointly form a trimethylene or tetramethylene bridge.

"Sulpho" is to be understood as the radical $-SO_3M$ wherein M represents hydrogen or a salt-forming cation. Suitable salt-forming cations M are, in general, those of alkaline earth metals, for example of calcium, barium or magnesium and particularly of alkali metals, for example of sodium or potassium, but also ammonium optionally substituted by alkyl or hydroxyalkyl having 1 to 4 carbon atoms, or amine salt ions of cyclic amines, such as pyridine, morpholine, piperidine and the like. Besides hydrogen, the potassium cation and the sodium cation are particularly preferred in the meaning of M.

Within the scope of formula (1), compounds of interest are above all those of the formula

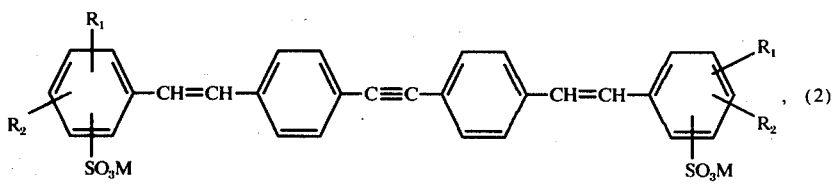

wherein M denotes hydrogen or a salt-forming cation, $R_1$ denotes hydrogen, chlorine, alkyl having 1 to 4 carbon atoms or alkoxy having 1 to 4 carbon atoms, or, conjointly with $R_2$, denotes trimethylene or tetramethylene located in the 3,4-position, and $R_2$ denotes hydrogen, chlorine or alkoxy having 1 to 4 carbon atoms (preferably methoxy) or, conjointly with $R_1$, denotes trimethylene or tetramethylene located in the 3,4-position.

Compounds of particular practical interest correspond to the formula.

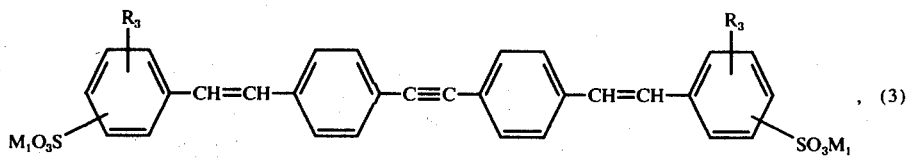

wherein $M_1$ denotes a hydrogen ion, alkali metal ion, alkaline earth metal ion, ammonium ion or amine salt ion, and $R_3$ denotes hydrogen or alkoxy having 1 to 4 carbon atoms.

The present invention relates further to a process for the manufacture of the new compounds of the formulae (1) to (3).

Various processes for the manufacture of stilbene compounds are already known. One such process, which is widely applicable, has been disclosed under the name "anil synthesis" [compare, for example, Helvetica Chimica Acta 50 (1967), 906 et seq. and 52 (1969), 2521 et seq.]. Hitherto, however, the absence from the reactants of substituents capable of salt-formation, such as, for example, the sulpho group, has been quoted as a condition for the anil synthesis to take place [compare Helvetica Chimica Acta 50 (1967), 912 and 52 (1969), 2524].

It has now been found, surprisingly, that stilbene compounds containing sulpho groups can also be manufactured in good yields by means of the anil synthesis. This process makes it possible to manufacture the new compound particularly conveniently.

The manufacture, in accordance with the invention, of the compounds of the formula (1) is characterised in that 1 mol of a 4,4'-dimethyltolane derivative of the formula

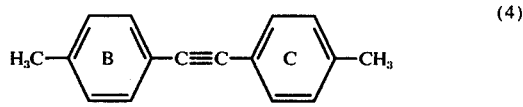

is reacted, in the presence of a strongly basic alkali compound in a, preferably strongly polar, neutral to basic organic solvent, with 2 mols of an anil of the formula

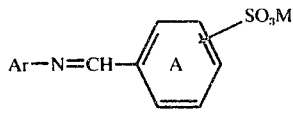  (5)

wherein Ar denotes an unsubstituted or substituted aromatic radical.

Correspondingly, the manufacture of the tolane derivatives of the formulae (2) and (3) is carried out by reacting 4,4'-dimethyltolane with an anil of the formula

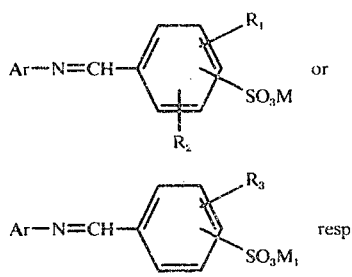

respectively.

The aromatic radical Ar is generally composed of one or more six-membered carbocyclic structures, and it preferably denotes an unsubstituted or substituted naphthyl or phenyl radical, particularly a phenyl radical which is unsubstituted or substituted by chlorine.

The starting materials for the manufacture of the new compounds of the formulae (1) to (3), that is to say the compounds of the formulae (4) to (7), are known or are manufactured in analogy to processes which are in themselves known.

The reaction with the anils can be carried out in the presence of a suitable, preferably strongly polar, neutral to alkaline organic solvent which is free from atoms, particularly hydrogen atoms, which can be replaced by alkali metals. In practice, possible solvents of this kind are, above all, dialkylamides of formic acid and phosphoric acid and tetraalkylureas, "alkyl" denoting a lower alkyl group containing 1 to 4 carbon atoms, particularly a methyl group. The following should be mentioned as important representatives of such solvents: diethylformamide, hexamethylphosphoric acid triamide, tetramethylurea and especially dimethylformamide. Mixtures of solvents are also possible.

Furthermore, as mentioned, a strongly basic alkali metal compound is necessary for the reaction. Depending on the nature of the solvent and the reactivity of the anil employed, certain sodium alcoholates, such as sodium t-butylate, and, particularly, potassium compounds of the composition $$KOC_{m-1}H_{2m-1}$$

wherein $m$ represents an integer from 1 to 6, preferably 2 to 6, such as, for example, potassium hydroxide or, particularly, potassium tert.-butylate, are suitable for this purpose. In the case of such alkali metal alcoholates the reaction must be carried out in a virtually anhydrous medium, while in the case of potassium hydroxide a small water content of up to about 15% (for example contained in water of crystallisation) is still allowable. Potassium hydroxide or sodium t-butylate are advantageously used, for example, in combination with hexamethylphosphoric acid triamide.

Theoretically, the dimethyltolane is reacted with the anils in equivalent quantities, that is to say in a molar ratio of 1:2. However, an excess of anil up to approximatly 50% is generally suitable. It is advantageous to use at least an equivalent quantity of the alkali metal compound, that is to say at least 1 mol of a compound having, for example, one KO group, to one mol of anil. When potassium hydroxide is used, it is advantageous to use a four-fold to eight-fold quantity. Particularly good yields are obtained when using potassium tert.-butylate in a quantity which is one to six times, preferably two to four times, the equivalent quantity.

The reaction according to the invention can generally be carried out at temperatures in the range between about 10 and 150° C. With particularly reactive anils, the reaction takes place even at room temperature, in which case no external supply of heat is necessary. This is particularly advantageous if the reactants contain ring compounds or substituents which are easily opened or split off respectively or modified chemically in some other way, by alkali. This is true, for example, for anils with chlorine substituents which can be split off easily. It is most advantageous, however, to carry out the reaction at elevated temperature. For example, the reaction mixture is warmed slowly to 30° to 80° C and is then kept at this temperature for some time, for example ½ to 2 hours. The manufacture of the anil and its reaction with the tolane compound can also be carried out in a onepot process. For example, an aldehyde is heated with an excess of aniline in dimethylformamide, the mixture is evaporated completely in vacuo, the tolane component and dimethylformamide are added and the customary procedure is followed. The end products can be worked up from the reaction mixture by customary methods which are in themselves known. Isolation is carried out, for example, by precipitation with water, or in the case of water-soluble products, by salting out, for example using NaCl or KCl, or by neutralisation, where appropriate by acidification with a strong mineral acid, such as, for example, HCl, it being sometimes possible in this last case to precipitate the free sulphonic acids. These can optionally be converted into the corresponding alkali metal salts, alkaline earth metal salts, ammonium salts or amine salts by reaction with alkali metal salts or alkaline earth metal salts or with ammonium hydroxide or amines. The amine salts of the sulphonic acids are also obtained, for example, by converting an alkali metal salt of the sulphonic acid into the sulphochloride by means of phosphorus oxychloride, thionyl chloride, phosphorus pentachloride and the like and subsequent saponification in the presence of the desired amine.

The invention also relates to a process for the manufacture of compounds of the formula (1), which process is characterised in that 2 mols of an anil of the formula

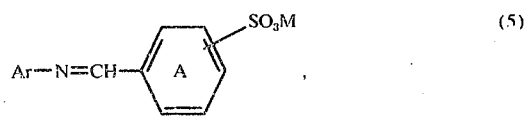  (5)

wherein A, Ar and M have the meaning given in the preceding text, are reacted with one mol of a compound which, under the conditions of the anil synthesis, gives a 4,4'-dimethyltolane derivative of the formula

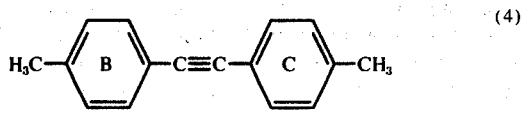

Examples of possible compounds which give a derivative of the formula (4), are those of the formula

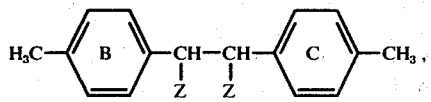

wherein Z denotes chlorine, bromine or iodine.

The new compounds defined above show a more or less pronounced fluorescence in the dissolved or finely divided state. They can be used for the optical brightening of the most diverse synthetic, semi-synthetic or natural organic materials or substances which contain such organic materials.

The following groups of organic materials, where optical brightening thereof is relevant, may be mentioned as examples of the above, without the survey given below being intended to express any restriction thereto:

I. Synthetic organic high molecular materials:

a. Polymerisation products based on organic compounds containing at least one polymerisable carbon-carbon double bond, that is to say their homopolymers or copolymers as well as their after-treatment products such as, for example, cross-linking, grafting or degradation products, polymer blends or products obtained by modification of reactive groups, for example polymers based on $\alpha,\beta$-unsaturated carboxylic acids or derivatives of such carboxylic acids, especially on acrylic compounds (such as, for example, acrylic esters, acrylic acid, acrylonitrile, acrylamides and their derivatives or their methacrylic analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride).

b. Polymerisation products, such as are obtainable by ring opening, for example, polyamides of the polycaprolactam type, and also polymers which are obtainable both via polyaddition and via polycondensation, such as polyethers or polyacetals.

c. Polycondensation products or precondensates based on bifunctional or polyfunctional compounds possessing condensable groups, their homocondensation and co-condensation products, and after-treatment products, such as, for example, polyesters, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols, such as, for example alkyd resins) polyesters, polyamides (for example hexamethylenediamine adipate), maleate resins, melamine resins, their precondensates and analogues, polycarbonates and silicones.

d. Polyaddition products, such as polyurethanes (cross-linked and non-crosslinked) and epoxide resins.

II. Semi-synthetic organic materials, for example, cellulose esters of varying degrees of esterification (so-called 2½-acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and casein.

The organic materials to be optically brighened can be in the most diverse states of processing (raw materials, semi-finished goods or finished goods). On the other hand, they can be in the form of structures of the most diverse shapes, say for example predominantly three-dimensional bodies such as sheets, profiles, injection mouldings, various machined articles, chips, granules or foams, and also as predominantly two-dimensional bodies such as films, sheets, lacquers, coverings, impregnations and coatings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of continuous filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboards or paper pulps.

The compounds to be used according to the invention are of importance, inter alia, for the treatment of organic textile materials, especially woven textile fabrics. Where fibres, which can be in the form of staple fibres or continuous filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140° C, for example at the boiling point of the bath or near it (about 90° C). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brighteners according to the present invention can, for example, also be employed in the following use forms:

a. Mixed with dyestuffs (shading) or pigments (coloured pigments or especially, for example, white pigments), or as an additive to dye baths, printing pastes, discharge pastes or reserve pastes, or for the aftertreatment of dyeings, prints or discharge prints.

b. Mixed with so-called "carriers", wetting agents, plasticisers, swelling agents, anti-oxidants, light stabilisers, heat stabilisers and chemical bleaching agents (chlorite bleach or bleaching bath additives).

c. Mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes, anti-soiling finishes or anti-static finishes or antimicrobial finishes.

d. Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather.

e. As additives to so-called "master-batches".

f. As additives to the most diverse industrial products in order to render these more marketable (for example improving the appearance of soaps, detergents or pigments).

g. In combination with other optically brightening substances.

h. In spinning bath preparations, that is to say as additives to spinning baths such as are used for improving the slip for the further processing of synthetic fibres, or from a special bath before the stretching of the fibre.

i. As scintillators, for various purposes of a photographic nature, such as, for example for electrophotographic reproduction or supersensitisation, and for the optical brightening of photographic layers, optionally in combination with white pigments such as, for example, $TiO_2$.

If the brightening process is combined with textile treatment methods or finishing methods, the combined treatment can in many cases advantageously be carried out with the aid of appropriate stable preparations, which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a series of fibre substrates, for example polyester fibres, with the brighteners according to the invention, is to impregnate these fibres with the aqueous dispersions (or optionally also solutions) of the brighteners at temperatures below 75° C, for example at room temperature, and to subject them to a dry heat treatment at temperatures above 100° C, it being generally advisable additionally to dry the fibre material beforehand at a moderately elevated temperature, for example at not less than 60° C and up to about 130° C. The heat treatment in the dry state is then advantageously carried out at temperatures between 120° and 225° C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 0.8 percent by weight and optionally of up to about 2 percent by weight can be employed. For most practical purposes, amounts between 0.0005 and 0.5 percent by weight are of preferred interest.

The new optical brightening agents are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying to the washing powder, or during the preparation of liquid washing agent combinations. They can be added either in the form of a solution or dispersion in water or other solvents or, without auxiliaries, as a dry brightening powder. For example, the brightening agents can be mixed, kneaded or ground with the detergent substances and, in this form, admixed to the finished washing powder. However, they can also be sprayed in a dissolved or predispersed form onto the finished washing agent.

Possible washing agents are the known mixtures of detergent substances such as, for example, soap in the form of chips and powders, synthetics, soluble salts of sulphuric acid half esters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerolsulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminotetraacetic acid, and foam stabilisers, such as alkanolamides of higher fatty acids. The washing agents can further contain for example: antistatic agents, skin protection agents which restore fat, such as lanolin, enzymes, antimicrobial agents, perfumes and dyestuffs.

of a 1% strength aqueous potassium chloride solution, with the aid of 0.5 g of active charcoal.

The potassium/sodium salt of the formula

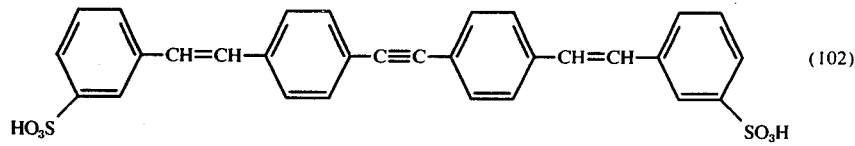

The new optical brighteners have the particular advantage that they are also active in the presence of active chlorine donors such as, for example, hypochlorite, and can be used without significant loss of the effects in wash liquors containing non-ionic washing agents, for example alkylphenol polyglycol esters.

The compounds according to the invention are added in amounts of 0.0005–1% or more, relative to the weight of the liquid or pulverulent finished washing agent. Wash liquors which contain the indicated amounts of the optical brighteners claimed impart a brilliant appearance in daylight when used to wash textiles of cellulose fibres, polyamide fibres, cellulose fibres with a high quality finish, polyester fibres, wool and the like.

The washing treatment is carried out as follows, for example:

The textiles indicated are treated for 1 to 30 minutes at 20° to 100° C in a wash liquor which contains 1 to 10 g/kg of a built-up composite washing agent and 0.05 to 1% relative to weight of the washing agent, of the claimed brightening agents. The liquor ratio can be 1:3 to 1:50. After washing, the textiles are rinsed and dried in the usual manner. The wash liquor can contain 0.2 g/l of active chlorine (for example as hypochlorite) or 0.1 to 2 g/l of sodium perborate as a bleaching additive.

In the examples, unless otherwise stated, percentages are always percentages by weight. Unless otherwise noted, melting points and boiling points are uncorrected.

EXAMPLE 1

22.4 g of potassium t-butylate are introduced, while stirring and passing in nitrogen, into a solution of 5.15 g of 4,4'-dimethyltolane and 15.6 g of the sodium salt of o-benzaldehydesulphonic acid anil in 80 ml of anhydrous dimethylformamide at 50° C. The temperature is allowed to rise to 60° C and the mixture is kept for one hour at 60° C and for one hour at 80° C and is cooled in an ice bath. A solution of 20 g of potassium chloride in 400 ml of water is added to the violet reaction mixture, and the precipitated product is filtered off, washed with 3% strength aqueous potassium chloride solution and dried in vacuo at 100° C. This gives 10.3 g (about 65% of theory) of the crude disulphonic acid of the formula is obtained in an almost quantitative yield in an analogous manner as a light yellow powder, which recrystallised from a fairly large volume of 7:5 dimethylformamide-water.

The anil required for the preparation of the compound of the formula (101) is obtained as follows: 208 g of the crude sodium salt of o-sulphobenzaldehyde are briefly boiled up in 1,040 ml of ethylene glycol monomethyl ether and the solution is clarified by filtration at room temperature in order to remove insoluble salts. 93.1 g of freshly distilled aniline are added to the filtrate and the mixture is heated for one hour at reflux temperature and filtered again from precipitated salts. 300 ml are now first distilled off at atmospheric pressure and then the remainder of the solvent is distilled off under reduced pressure. The residue is crystallised from one liter of n-butanol, filtered off and dried at 100° C in vacuo.

This gives 152 g of a colourless, hydgroscopic product of the formula

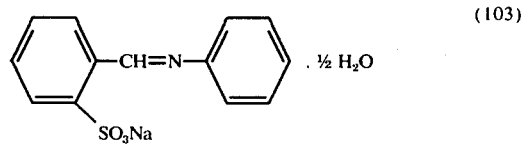

(after recrystallisation from n-butanol). This anil is obtained in an even simpler manner by using, instead of ethylene glycol monomethyl ether, 1.2 l of n-butanol, from which it crystallises out on cooling.

The sodium salt of m-benzaldehydesulphonic acid anil which is requied for the preparation of the compound of the formula (102), is obtained in an analogous manner. It is isolated by boiling up in ethanol (instead of n-butanol) the residue obtained after the distillation of the solvent and filtering off, at room temperature, the anil which is insoluble therein, washing it with ethanol and drying.

If 4,4'-dimethyltolane is reacted with the calcium salt (instead of the sodium salt) of o-benzaldehydesulphonic acid anil, the corresponding calcium salt is obtained. The calcium salt of o-benzaldehydesulphonic acid anil is obtained by introducing the compound of the formula (103) into an aqueous solution of calcium

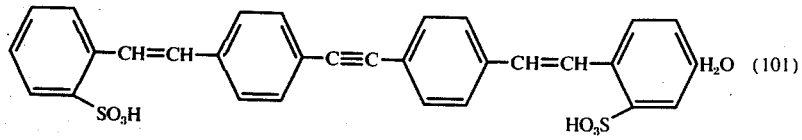

as a light yellow, hygroscopic potassium salt, mixed with some sodium salt. It is recrystallised from 250 ml chloride, from which it crystallises.

EXAMPLE 2

The compound of the formula (101) is obtained in accordance with Example 1, but the p-chloroanil of the formula

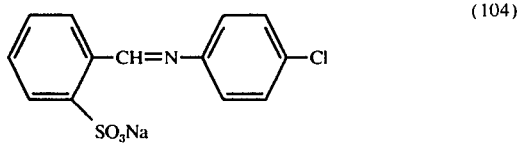 (104)

is used as the anil component.

In order to prepare this compound, 223 g of the sodium salt of o-sulphobenzaldehyde in 480 g of p-chloroaniline are heated slowly, with stirring, to 185° C and the reaction mass, which has become liquid, is kept at this temperature for ½ hour. After cooling to approx. 130° C, 2 l of n-butanol are added and the mixture is filtered hot and allowed to cool to 0° C. The precipitate is filtered off with suction, washed with twice 200 ml of n-butanol and dried at 100° C in vaccuo. Yield 216 g, melting point approx. 239° C after recrystallisation from n-butanol. Further product can be additionally obtained by concentrating the mother liquor.

EXAMPLE 3

The procedure is essentially in accordance with Example 1, using the corresponding aldehyde anils and only 16.8 g of potassium t-butylate. Thus the tolanes of the general formula (105), listed in the table which follows, are obtained, principally in the form of their potassium and/or sodium salts, under the conditions indicated.

Compound (107): from 2-chloro-benzaldehyde-5-sulphonic acid (K salt) analogously to m-benzaldehydesulphonic acid anil (K salt), (see Example 1).

Compound (108): boiling up 15.8 g of 2-methoxybenzaldehydesulphonic acid (Na salt) in 100 ml of aniline and 23 ml of dimethylformamide, distilling off 30 ml of solvent and cooling.

Compound (109): 62.5 g of the crude sodium salt of p-sulphobenzaldehyde are briefly boiled up in 500 ml of dimethylformamide and the solution is clarified by filtration at room temperature, in order to remove insoluble salts. 28 g of aniline are added to the filtrate and it is heated for 10 minutes to the boil, in the course of which the anil already crystallises out. 200 ml of solvent are distilled off, and the mixture is cooled and filtered and the residue is washed with 50 ml of dimethylformamide and with twice 50 ml of methanol. This gives 51.3 g of colourless crystals.

Compound (110): heating 2,3-dimethoxy-5-sulphobenzaldehyde (K salt) with aniline (a 10% excess) in ethanol under reflux. The diluted solution is clarified by hot filtration, concentrated and cooled.

Compound (111): from 3-methyl-5-sulphobenzaldehyde (K salt) as before.

EXAMPLE 4

5.15 g of 4,4'-dimethyltolane are reacted with 15.6 g of m-benzaldehydesulphonic acid anil in 80 ml of hexamethylphosphoric acid triamide in the presence of 24.9 g of 90% strength powdered potassium hydroxide for 2 1/2 hours at 90° C in accordance with Example 1. After isolating and extracting by boiling with chloroform in a corresponding manner, 2.5 g of the compound of the formula (102) are obtained as the K/Na salt.

TABLE

| Formula No. | $U_2 / U'_2$ | $U_3 / U'_3$ | $U_4 / U'_4$ | $U_5 / U'_5$ |
|---|---|---|---|---|
| 106 | H | SO$_3$H | Cl | H |
| 107 | Cl | H | H | SO$_3$H |
| 108 | OCH$_3$ | H | H | SO$_3$H |
| 109 | H | H | SO$_3$H | H |
| 110 | OCH$_3$ | OCH$_3$ | H | SO$_3$H |
| 111 | H | SO$_3$H | H | CH$_3$ |

In order to prepare the chlorine-containing tolanes of the formula (106) and (107), the reaction is carried out at room temperature. The crude products of the general formula (105) are purified, for example, by extracting by boiling with chloroform and recrystallising or extracting by boiling (depending on the solubility) with water, aqueous potassium chloride solution, n-propanol-water, ethylene glycol monomethyl ether, dimethylformamide, dimethylformamide-water, dimethylsulphoxide or dimethylsulphoxide-water.

The anils required as starting products for the preparation of the tolane compounds quoted in the table are obtained as follows:

Compound (106): boiling up 4-chloro-benzaldehyde-3-sulphonic acid (Na salt) with 10% excess aniline in ethanol, cooling and filtering off with suction.

EXAMPLE 5

11.0 g of crude product of the formula (109) are stirred in 100 ml of trichlorobenzene, 8 ml of thionyl chloride and 1 ml of dimethylformamide for about 2 hours under reflux. The solution is clarified by hot filtration, whereupon the disulphochloride crystallises on cooling (melting point 360° C after recrystallisation from trichlorobenzene).

3.0 g of disulphochloride in 20 ml of dimethylform-amide and 1 ml of water are heated under reflux for ½ hour. The solution is completely evaproated in vacuo, the residue is taken up in a lower alcohol and the mixture is filtered at room temperature. After washing with ethanol and recrystallising from n-propanol-water, the bis-dimethylamine salt of the formula

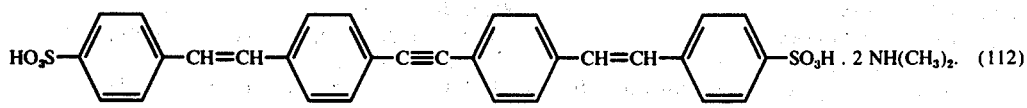

is obtained.

EXAMPLE 6

22.4 g of potassium t-butylate are introduced, while stirring and passing in nitrogen, into a solution of 9.2 g of the compound of the formula

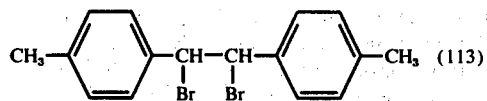

and 15.6 g of the sodium salt of m-benzaldehydesulphonic acid anil in 150 ml of dimethylformamide at 60° C. The temperature is allowed to rise to 80° C and the mixture is kept at 80° C for 1 hour and is cooled in an ice bath. 300 ml of water are added to the violet reaction mixture and the precipitated product is filtered off, washed with water until neutral and dried in vacuo at 100° C. After extraction by boiling with 140 ml of chloroform, 12.9 g (83% of theory) of the compound of the formula (102) are obtained.

EXAMPLE 7

Bleached cotton material is washed for 15 minutes, using a liquor ratio of 1:20, in a liquor warmed to 60° C which contains the following additives per liter:
 0.004 g of the brightener of the formula (101), (102), (106), (107) or (108),
 0.25 g of active chlorine (Javelle water) and
 4 g of a washing powder of the following composition:
  15.00% of dodecylbenzenesulphonate,
  10.00% of sodium laurylsulphonate,
  40.00% of sodium tripolyphosphate,
  25.75% of anhydrous sodium sulphate,
  7.00% of sodium metasilicate,
  2.00% of carboxymethylcellulose and
  0.25% of ethylenediaminetetraacetic acid.

The cotton material is only introduced into the bath 15 minutes after the preparation of the washing liquor warmed to 60° C. After rinsing and drying, the woven fabric exhibits a good brightening effect with good fastness to acid, light and chlorine. Good brightening effects are also obtained if the washing process is carried out in the same manner at 30° C.

The washing powder of the abovementioned composition can also contain the brightener of the formula (101), (102), (106), (107) or (108) directly incorporated.

EXAMPLE 8

A polyamide fibre woven fabric (Perlon) is introduced using a liquor ratio of 1:40 and at 60° C, into a bath which contains (relative to the weight of the material) 0.05% of a brightener of the formula (101), (102), (106), (107) or (108) and, per liter, 1 g of 80% strength acetic acid and 0.25 g of an addition reaction product of 30 to 35 mols of ethylene oxide with one mol of technical stearyl alcohol. The bath is warmed to the boil over the course of 30 minutes and is kept at the boil for 30 minutes. After rinsing and drying, a good brightening effect is obtained.

Similar brightening effects are obtained if, instead of the woven fabric of polyamide 6, a woven fabric of polyamide 66 (nylon) is used.

Finally, it is also possible to work under high temperature conditions, for example for 30 minutes at 130° C. The addition of 3 g/l of hydrosulphite is advisable for this method of application.

EXAMPLE 9

Bleached cotton material is washed for 30 minutes at 95° C, using a liquor ratio of 1:20. The washing liquor contains the following additives per liter:
 0.004 g of the brightener of the formulae (101), (102), (106), (107) or (108) and
 4 g of a washing powder of the following composition:
  40.0% of soapflakes,
  15.0% of sodium tripolyphosphate,
  8.0% of sodium perborate,
  1.0% of magnesium silicate,
  11.0% of sodium metasilicate (9 $H_2O$),
  24.6% of calcined sodium carbonate and
  0.4% of ethylenediaminetetraacetic acid.

After rinsing and drying, the cotton woven fabric exhibits a strong brightening effect.

EXAMPLE 10

An article of cotton material, given a non-iron finish by means of an aminoplast resin, is washed for 15 minutes, using a liquor ratio of 1:20, in a liquor warmed to 55° C and containing the following additives per liter:
 0.004 to 0.0016 g of a brightener of the formulae (101), (102), (107) or (108) and
 4 g of a washing powder of the following composition:
  15.00% of dodecylbenzenesulphonate,
  10.00% of sodium laurylsulphonate,
  40.00% of sodium tripolyphosphate,
  25.75% of anhydrous sodium sulphate,
  7.00% of sodium metasilicate,
  2.00% of carboxymethylcellulose and
  0.25% of ethylenediaminetetraacetic acid.

After rinsing and drying, the woven fabric exhibits a strong brightening effect with good fastness to light.

EXAMPLE 11

A polyamide fibre woven fabric (Perlon-Helanca) is washed for 15 minutes, using a liquor ratio of 1:20, in a liquor warmed to 55° C and containing the following additives per liter:
 0.004 to 0.016 g of a brightener of the formulae (101), (102) or (107),
 0.25 g of active chlorine (Javelle water) and
 4 g of a washing powder of the following composition:
  15.00% of dodecylbenzenesulphonate,
  10.00% of sodium laurylsulphonate,
  40.00% of sodium tripolyphosphate, 25.75% of anhydrous sodium sulphate,
7.00% of sodium metasilicate,
2.00% of carboxymethylcellulose and
0.25% of ethylenediaminetetraacetic acid.

The polyamide fibre woven fabric is not introduced into the washing liquor, warmed to 55° C, until 15 minutes after the latter has been prepared. After rinsing and drying, the woven fabric exhibits a good brightening effect with good fastness to light.

A good brightening effect is also obtained, if the washing process is carried out in the same manner, but at 25° C.

The washing powder of the abovementioned composition can also contain the brighteners of the formulae designated above, directly incorporated.

EXAMPLE 12

An aqueous suspension of 100 parts of cellulose in 4,000 parts of water is mixed for 15 minutes in a hollander with an aqueous solution of 0.1 part of the brightener of the formula (101), two parts of resin suspension and 3 parts of aluminium sulphate are added and the mixture is diluted with 20,000 parts of recovered water containing 1 g of aluminium sulphate per litre, and is converted in the customary manner into paper sheets. The paper sheets are strongly brightened.

EXAMPLE 13

2 g of the optical brightener of the formula (101) are dissolved in approx. 50 ml of hot, distilled water. At the same time 80 g of a degraded starch are dissolved to form a colloidal solution in 1,000 ml of hot water at 90° C. The brightener solution is then incorporated into the starch solution. The resulting solution can have a pH value of 5.5 to 7.

A sized printing paper is coated on the surface with this sizing liquor in a sizing press and the coated paper is dried at about 90°–120° C in the drying section of the paper machine.

This gives a paper with a significantly improved degree of whiteness.

Similarly good results are obtained using a pigment coating liquor or a synthetic resin dispersion containing aluminium magnesium silicate.

EXAMPLE 14

A casting composition consisting of 10 g of polyacrylonitrile, 0.2 g of titanium dioxide (anatase modification) as a delustering agent, and 40 ml of dimethylformamide which contains 5 mg of one of the compounds of the formulae (106) or (107), is cast on a glass plate and is drawn out by means of a metal rod to form a thin film.

After drying the sheet is strongly brightened.

What I claim is:

1. A tolane compound of the formula

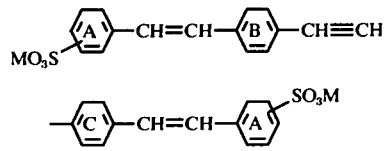

wherein
M denotes hydrogen or a salt-forming cation and the benzene nuclei A, B and C can contain non-chromophoric substituents selected from the group consisting of alkyl having 1 to 4 carbon atoms, chlorine, alkoxy having 1 to 4 carbon atoms, phenoxy, alkylmercapto having 1 to 4 carbon atoms, phenylmercapto, sulpho, trimethylene and tetramethylene, said trimethylene and tetramethylene substituents being attached to two adjacent carbon atoms of the benzenoid ring.

2. A tolane compound according to claim 1, corresponding to the formula

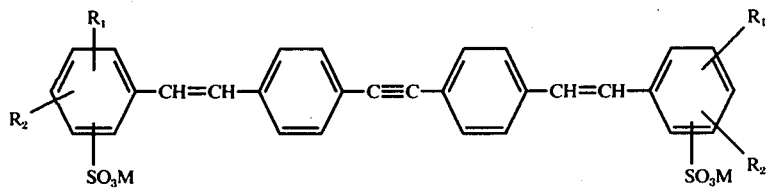

wherein M denotes hydrogen or a salt-forming cation, $R_1$ denotes hydrogen, chlorine, alkyl having 1 to 4 carbon atoms or alkoxy having 1 to 4 carbon atoms, or, conjointly with $R_2$, denotes trimethylene or tetramethylene located in the 3,4-position, and $R_2$ denotes hydrogen or alkoxy having 1 to 4 carbon atoms, or, conjointly with $R_1$, denotes trimethylene or tetramethylene located in the 3,4-position.

3. A tolane compound according to claim 1, corresponding to the formula

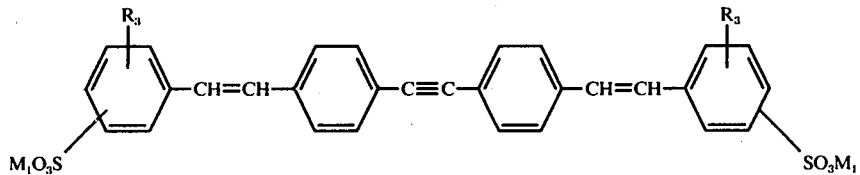

wherein $M_1$ denotes a hydrogen ion, alkali metal ion, alkaline earth metal ion, ammonium ion or amine salt ion, and $R_3$ denotes hydrogen or alkoxy having 1 to 4 carbon atoms.

4. In a process for optically brightening organic materials, the improvement which comprises incorporating in the materials to be optically brightened or applying to the surface of the materials to be optically brightened a tolane compound as defined in claim 1.

5. Process according to claim 4, for optically brightening polyamides and cellulose.

6. Process according to claim 4, wherein 0.0001 to 1 percent by weight, calculated on the total quantity of organic material, of a tolane compound as defined in claim 1 is used.

* * * * *